US009232898B2

(12) United States Patent
Spear et al.

(10) Patent No.: US 9,232,898 B2
(45) Date of Patent: Jan. 12, 2016

(54) METHOD AND APPARATUS TO MANAGE LEAD-RELATED CONDITIONS FOR FAULT TOLERANCE ENHANCEMENTS

(71) Applicant: Medtronic, Inc., Minneapolis, MN (US)

(72) Inventors: Thomas H. Spear, Bloomington, MN (US); Nancy M. Germanson, Maple Grove, MN (US)

(73) Assignee: Medtronic, Inc., Minneapolis, MN (US)

( * ) Notice: Subject to any disclaimer, the term of this patent is extended or adjusted under 35 U.S.C. 154(b) by 155 days.

(21) Appl. No.: 13/654,860

(22) Filed: Oct. 18, 2012

(65) Prior Publication Data

US 2013/0109939 A1     May 2, 2013

Related U.S. Application Data

(60) Provisional application No. 61/552,017, filed on Oct. 27, 2011.

(51) Int. Cl.
| | |
|---|---|
| *A61N 1/00* | (2006.01) |
| *A61B 5/0215* | (2006.01) |
| *A61N 1/39* | (2006.01) |

(Continued)

(52) U.S. Cl.
CPC ............... *A61B 5/0215* (2013.01); *A61B 5/042* (2013.01); *A61B 5/0452* (2013.01); *A61N 1/3706* (2013.01); *A61N 1/3937* (2013.01); *A61B 5/7217* (2013.01); *A61N 1/08* (2013.01); *A61N 1/3956* (2013.01)

(58) Field of Classification Search
CPC ........... A61M 1/00; A61M 3/00; A61M 9/00; A61N 1/00; A61N 1/02; A61N 1/04; A61N 1/08
See application file for complete search history.

(56) References Cited

U.S. PATENT DOCUMENTS

| | | |
|---|---|---|
| 3,888,261 A | 6/1975 | Mauer |
| 4,105,900 A | 8/1978 | Martin et al. |

(Continued)

FOREIGN PATENT DOCUMENTS

WO     2009082783     7/2009

OTHER PUBLICATIONS

Case Report, "Early Detection of Lead Fracture by Painless High Voltage Lead Impedance Measurement in a Transvenous ICD Lead System", by Jens Stevens MD., et al., Journal of Interventional Cardiac Electrophysiology 4, 269-272 (2000).

(Continued)

*Primary Examiner* — Christopher D Koharski
*Assistant Examiner* — Elizabeth K So
(74) *Attorney, Agent, or Firm* — Evans M. Mburu

(57) ABSTRACT

The disclosure describes systems, methods, and apparatus providing detection mechanism for lead-related conditions, including transient behaviors, on a conductive pathway of a medical electrical lead. In one example, a sense path arbitration module identifies a lead-related condition associated with a conductive pathway based on signal processing to identify transients emerging from a propagated signal. The sense path arbitration module may evaluate a plurality of conductive pathways of the medical electrical lead and arbitrates propagation of a sensed signal that is transmitted through the plurality of lead conductors based on the evaluation. Therapy delivery functions utilizing the medical electrical lead may also be controlled in response to the signal processing and identification of the lead-related condition on a conductive pathway.

12 Claims, 9 Drawing Sheets

(51) Int. Cl.
  *A61N 1/37*      (2006.01)
  *A61B 5/042*     (2006.01)
  *A61B 5/0452*    (2006.01)
  *A61N 1/08*      (2006.01)
  *A61B 5/00*      (2006.01)

(56) References Cited

U.S. PATENT DOCUMENTS

| | | |
|---|---|---|
| 4,140,131 A | 2/1979 | Dutcher et al. |
| 4,549,548 A | 10/1985 | Wittkampf et al. |
| 4,579,119 A | 4/1986 | Callaghan |
| 4,606,349 A | 8/1986 | Livingston et al. |
| 4,620,303 A | 10/1986 | Tschoepe |
| 4,899,750 A | 2/1990 | Ekwall |
| 4,916,612 A | 4/1990 | Chin et al. |
| 5,003,975 A | 4/1991 | Hafelfinger et al. |
| 5,117,824 A | 6/1992 | Keimel et al. |
| 5,137,021 A | 8/1992 | Wayne et al. |
| 5,156,149 A | 10/1992 | Hudrlik |
| 5,184,614 A | 2/1993 | Collins et al. |
| 5,201,808 A | 4/1993 | Steinhaus et al. |
| 5,201,865 A | 4/1993 | Kuehn |
| 5,224,475 A | 7/1993 | Berg et al. |
| 5,344,430 A | 9/1994 | Berg et al. |
| 5,350,410 A | 9/1994 | Kleks et al. |
| 5,402,070 A | 3/1995 | Shelton et al. |
| 5,431,692 A | 7/1995 | Hansen et al. |
| 5,453,468 A | 9/1995 | Mascia et al. |
| 5,507,786 A | 4/1996 | Morgan et al. |
| 5,534,018 A | 7/1996 | Wahlstrand et al. |
| 5,549,646 A | 8/1996 | Katz et al. |
| 5,722,997 A | 3/1998 | Nedungadi et al. |
| 5,741,311 A | 4/1998 | Mc Venes et al. |
| 5,755,742 A | 5/1998 | Schuelke et al. |
| 5,765,031 A | 6/1998 | Mimuth et al. |
| 5,814,088 A | 9/1998 | Paul et al. |
| 5,891,179 A | 4/1999 | Er et al. |
| 5,944,746 A | 8/1999 | Kroll |
| 6,052,753 A | 4/2000 | Doerenberg et al. |
| 6,445,951 B1 | 9/2002 | Mouchawar |
| 6,493,586 B1 | 12/2002 | Stahmann et al. |
| 6,721,600 B2 | 4/2004 | Jorgenson et al. |
| 6,859,667 B2 | 2/2005 | Goode |
| 6,871,091 B2 | 3/2005 | Wilkinson et al. |
| 7,047,083 B2 | 5/2006 | Gunderson et al. |
| 7,149,580 B2 | 12/2006 | Conley et al. |
| 7,225,025 B2 | 5/2007 | Goode |
| 7,236,834 B2 | 6/2007 | Christopherson et al. |
| 7,389,144 B1 | 6/2008 | Osorio et al. |
| 7,515,961 B2 | 4/2009 | Germanson et al. |
| 2003/0204233 A1 | 10/2003 | Laske et al. |
| 2005/0043768 A1 | 2/2005 | Goode |
| 2005/0090870 A1 | 4/2005 | Hine et al. |
| 2006/0064149 A1 | 3/2006 | Belacazar et al. |
| 2007/0265674 A1 | 11/2007 | Olson et al. |
| 2010/0027176 A1 | 2/2010 | Kawate et al. |
| 2010/0063561 A1* | 3/2010 | Sloman et al. .......... 607/27 |
| 2010/0217366 A1 | 8/2010 | Moulder et al. |
| 2011/0054554 A1 | 3/2011 | Swerdlow |

OTHER PUBLICATIONS

NASA Office of Logic Design, "Fault Tolerant Design", Preferred Reliability Practices No. PD-ED-1246, Sep. 21, 1995, pp. 1-4.
Avizienis et al., "Basic Concepts and Taxonomy of Dependable and Secure Computing", IEEE Transactions on Dependable and Secure Computing, vol. 1, No. 1, Jan.-Mar. 2004, pp. 11-33.
Avizienis, "Toward Systematic Design of Fault-Tolerant Systems", IEEE, Apr. 1997, pp. 51-58.
Dorwarth et al., "Transvenous Defibrillation Leads: High Incidence of Failure During Long-Term Follow-Up", J. Cardiovascular Electrophysiol., Vol. 14, Jan. 2003, pp. 38-43.
U.S. Appl. No. 13/014,965 entitled "Isolating Lead Conductor for Fault Detection", filed Jan. 27, 2011.
U.S. Appl. No. 13/015,042, entitled "Isolated Lead Conductor Measurements for Fault Detection", filed Jan. 27, 2011.
U.S. Appl. No. 13/156,632 entitled "Fault Tolerant Methods and Architectures for Embedded Intelligence in Medical Leads", filed Jun. 9, 2011.
U.S. Appl. No. 13/156,660, entitled "Method and Apparatus to Manage Lead-Related Conditions for Fault Tolerance Enhancements", filed Jun. 9, 2011.
The application is also related to U.S. Appl. No. 13/156,632 entitled "Isolated Lead Insulation Measurements for Fault Detection", filed Jul. 8, 2011.

* cited by examiner

METHOD AND APPARATUS TO MANAGE LEAD-RELATED CONDITIONS FOR FAULT TOLERANCE ENHANCEMENTS

CROSS-REFERENCE TO RELATED APPLICATIONS

This patent application is related U.S. patent application Ser. No. 13/014,965 entitled "ISOLATING LEAD CONDUCTOR FOR FAULT DETECTION" (P0033896.00) and U.S. patent application Ser. No. 13/015,042, entitled "ISOLATED LEAD CONDUCTOR MEASUREMENTS FOR FAULT DETECTION" (P0033896.01) both filed on Jan. 27, 2011 and both of which are incorporated herein by reference in their entirety. The application is also related to U.S. patent application Ser. No. 13/156,632 entitled "FAULT TOLERANT METHODS AND ARCHITECTURES FOR EMBEDDED INTELLIGENCE IN MEDICAL LEADS" (P0035462.00) and U.S. patent application Ser. No. 13/156,660, entitled "METHOD AND APPARATUS TO MANAGE LEAD-RELATED CONDITIONS FOR FAULT TOLERANCE ENHANCEMENTS" (P0036284.00) both filed on Jun. 9, 2011 and both of which are incorporated herein by reference in its entirety. The application is also related to U.S. patent application Ser. No. 13/156,632 entitled "ISOLATED LEAD INSULATION MEASUREMENTS FOR FAULT DETECTION" (P0041293.USU1) filed on Jul. 8, 2011 and incorporated herein by reference in its entirety.

FIELD

The present disclosure generally relates to implantable medical devices. More particularly, the disclosure pertains to a method and apparatus for detecting and managing static and transient behaviors, including continuous and real-time monitoring, associated with an implantable medical electrical lead to promote signal stability.

BACKGROUND

In the field of implantable medical devices, implantable cardioverter/defibrillators (ICD), implantable pulse generators (IPG) and pacemaker/cardioverter/defibrillators (PCD) provide sensing of arrhythmias and programmable staged therapies including pacing regimens and cardioversion energy and defibrillation energy shock regimens in order to terminate a sensed arrhythmia with the most energy efficient and minimally traumatic therapies. In such implantable medical devices, the atrial and ventricular pacing pulse generators, sense amplifiers and associated timing operations are incorporated into a system having atrial and ventricular pace/sense medical electrical leads.

A wide variety of such pace/sense and defibrillation leads have been proposed for positioning endocardially within a heart chamber or associated blood vessel or epicardially about the heart chambers or more remotely in subcutaneous locations. Typically, the leads bear pace/sense/defibrillation electrodes with associated lead conductors and connector elements all of which are either incorporated into a single pacing lead body or into a combined pacing and defibrillation lead body.

In such implantable medical device systems, the integrity of the medical electrical leads is of great importance. Generally, the leads are constructed of small diameter, highly flexible, lead bodies made to withstand the environmental effects of body fluids. In addition, the leads must be able to function in the presence of dynamic body environments that apply chemical and physical stress and strain to the lead body and the connections made to electrodes or sensor terminals. Some of these stresses may occur during the implantation process. Months or years later, porosity that developed from those stresses may be magnified by exposure to body fluids. These, in turn, may result in conductor or insulation related conditions that may be manifested in an intermittent or sudden Loss of Capture (LOC), out-of-range impedance and/or Loss of Sensing (LOS).

Lead insulation breaches, interior lead conductor wire fracture or fractures with other lead parts have been known to occur. In the U.S. patent application Ser. No. 13/156,660 assigned to the present assignee, the various issues affecting the lead conductive pathway, which is comprised of one or both the conductor and insulation, and resulting in partial or complete short or open circuits, for example, have been referred to, for simplicity, as "lead-related conditions." The Ser. No. 13/156,660 application explains that the lead-related conditions may manifest as static and/or intermittent/dynamic conductive discontinuities; a static conductive discontinuity may represent a conductive fracture resulting in conductor elements, such as filars or strands, being disconnected for an indefinite duration or until an intervention is performed while dynamic conductive discontinuity may represent a conductive fracture that results in transient or intermittent disconnections of the conductor elements for short durations in time. These lead-related conditions may lead to inappropriate implantable medical device responses if not mitigated or inhibited. For example, a transient that crosses the implantable medical device sense circuit thresholds may be misinterpreted as a physiological event. The perceived "physiological" event may lead to inappropriate implantable medical device algorithmic conclusions that may lead to undesired device operation.

Conventional approaches for detecting lead-related conditions have been limited to electrical behaviors leading to adverse system events. For example, filters have been employed in the sense circuits to eliminate high frequency signal components prior to threshold recognitions in the sense circuits. These filters may be designed to pass some frequency ranges and attenuate other frequency ranges and are effective for the frequency ranges they are designed to attenuate or pass, but are not consistently effective with signals or distortions that vary from those specified ranges. Several solutions have employed periodic testing that includes measurements of parameters such as lead impedance to determine when the integrity of the medical electrical lead is compromised. Other approaches to address lead body defects have been to construct the lead with re-engineered materials that are more robust.

However, there have been inherent limitations including expected and varying implant environmental conditions that eventually result in the emergence of lead-related conditions on the lead body. Another challenge associated with existing solutions is that the periodic measurements may not always correlate with the intermittent nature of the conductor make-break contact. Additionally, the periodic measurements and measurements triggered by apparent physiological signal aberrations may not identify lead-related conditions expeditiously for effective containment and to prevent error propagation.

As such, even with the robust lead body construction, there remains a need to provide for fault tolerant architectures including reconfiguration of lead functionality for continued system functionality and graceful degradation to promote safety.

SUMMARY

In general, exemplary embodiments of the present disclosure provide fault-tolerant architectures for medical electrical leads. The leads may utilize leading indicators and system critical indicators of a lead-related condition to perform reconfiguration of lead functionality based on changes in the lead electrical properties. In some embodiments, a lead monitoring system that may operate in a continuous, real-time manner may be utilized. The embodiments disclose methods and modules utilizing fault-tolerant architectures electrical transient recognition, containment and reconfiguration of a conductive pathway of the lead. The modules may be incorporated in the medical electrical lead, or a medical device coupled to the lead, or a combination of both the lead and the medical device.

In accordance with the foregoing, fault tolerant systems, devices and methods comprising an implantable medical device and a medical electrical lead may be provided. In one embodiment, a module may be provided having functionality to perform transient processing on a plurality of conductive pathways in a lead. The transient processing functionality may include transient recognition for detecting transient behaviors. The transient behaviors may include electrical characteristics that deviate from predetermined characteristics and are therefore capable of generating successive errors leading to an adverse system event.

In an embodiment, the module may also include containment circuitry for isolation of a conductive pathway on which the electrical transients or electrical patterns indicating non-physiological behaviors are detected. The containment may include decoupling the conductive pathway to prevent propagation of the signal to the implantable medical device sense circuitry. In response to detecting transient behavior on a given conductive pathway, the module may arbitrate the selection and propagation of electrical signals for therapy delivery or sensing functions by selecting another conductive pathway that does not exhibit the transient behavior. Arbitration in this context is deciding to choose one electrical conductive pathway rather than an alternative electrical conductive pathway based on a defined set of criteria.

In an embodiment, the lead includes a sense path arbitration module. The sense path arbitration module dynamically reconfigures the coupling of the plurality of the conductive pathways in response to detection of a transient on the pathways. In another embodiment, the sense path arbitration module dynamically reconfigures the coupling of the plurality of the conductive pathways in response to a comparative analysis of signals on the pathways.

In other embodiments, a threshold deviation module is provided for establishing one or more voltage reference levels for transient recognition. The one or more voltage reference levels may include a range having upper and lower threshold limits to facilitate distinction between various categories of lead-related conditions.

In another embodiment, a method is provided for detecting deviation characteristics in the conductive pathway behavior of a plurality of an implantable electrical lead's conductive pathways, arbitrating signal propagation through one of the conductive pathways and inhibiting the propagation of signals on a conductive pathway exhibiting the deviated behavior. The method may further include reconfiguration of the conductive pathway functionally to sustain medical functions including therapy delivery and sensing or to manage graceful degradation of the system. An additional aspect may include isolation of the conductive pathway exhibiting the deviated behavior.

The foregoing summary information is intended to merely illustrate some of the aspects and features of the present disclosure and is not meant to limit the scope in any way. In fact, upon review of the foregoing and the following described and depicted embodiments, one of skill in the art will surely recognize insubstantial modifications or extensions of the disclosure each of which is expressly intended to be covered hereby. The disclosure is also not limited to the specific-described embodiments; rather, the constituent elements in each embodiment may be combined as appropriate and the combination thereof may effectively serve as an embodiment of the present disclosure. Such embodiments along with modifications are also within the scope of the present disclosure.

BRIEF DESCRIPTION OF THE DRAWINGS

The following drawings are illustrative of particular embodiments of the present disclosure and therefore do not limit the scope of the disclosure. The drawings (not to scale) are intended for use in conjunction with the explanations in the following detailed description, wherein similar elements are designated by identical reference numerals. Moreover, the specific location of the various features is merely exemplary unless noted otherwise.

DETAILED DESCRIPTION

The following detailed description is merely exemplary in nature and is not intended to limit the disclosure or the application and uses of the disclosure. Furthermore, there is no intention to be bound by any expressed or implied theory presented in the preceding technical field, background, brief summary or the following detailed description.

For convenience, unless otherwise indicated the term "IMD" is inclusive of any implantable medical device capable of administering any of a number of therapies to the heart or other organs or other tissue of the patient. Illustrative embodiments of the present disclosure have been presented in the context of a cardiac pacemaker, it being understood that the disclosure certainly has applicability to many other types of IMDs. For convenience, a "medical electrical lead" as used herein defines a pace/sense/defibrillation electrode (including the case where the lead is only used for pacing, sensing, or defibrillation), a proximal end lead connector element for attachment to a terminal of an IMD, and a lead conductor within a lead body electrically connecting the pace/sense/defibrillation electrode and the lead connector element. The definition encompasses any combination of two or more pacing leads or defibrillation leads incorporated into the same lead body and any combinations of pacing lead(s) and defibrillation lead(s) in the same lead body.

As a brief overview, the disclosure pertains to a medical system having a medical electrical lead coupled to a medical device. The medical system includes a fault tolerant architecture for detecting a lead-related condition and dynamic reconfiguration for continued functionality in the presence of the lead-related condition.

Figure 1:
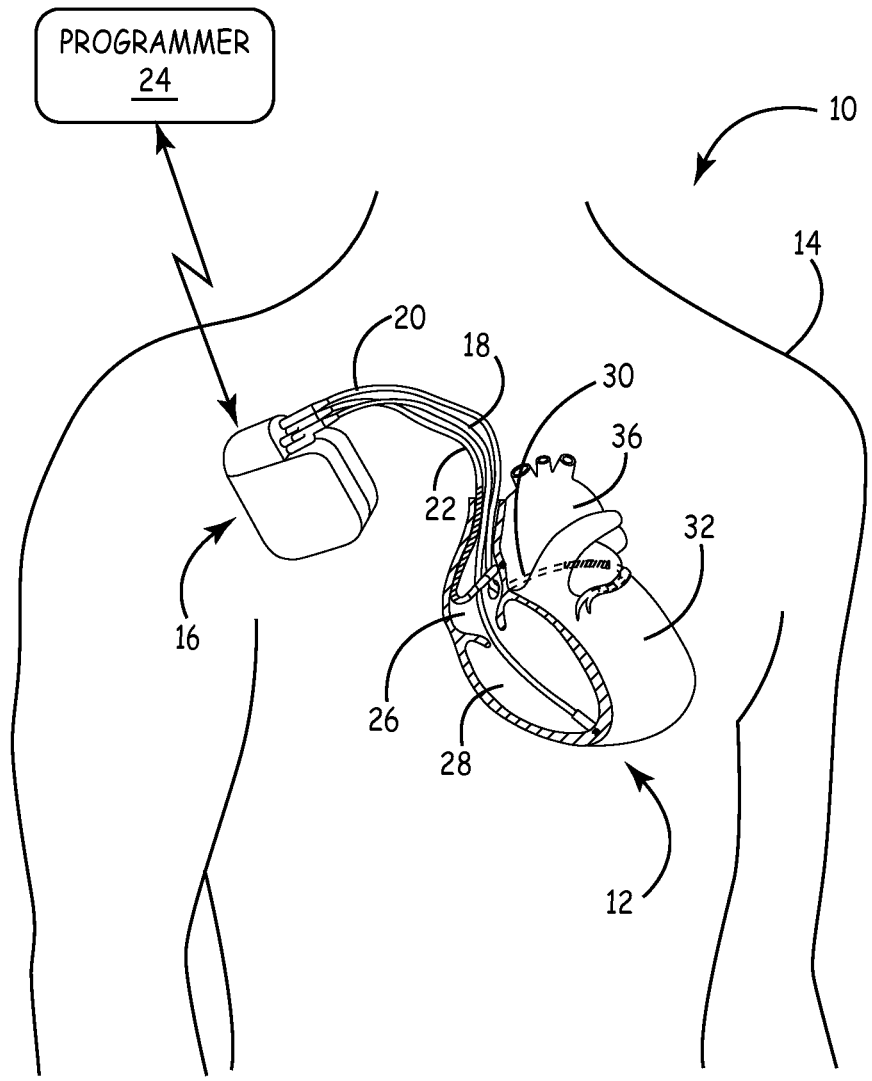
FIG. 1 is a conceptual diagram illustrating an example therapy system that may be used to provide therapy to a heart of a patient.

FIG. 1 is a conceptual diagram illustrating an example therapy system 10 that may be used to provide therapy to heart 12 of patient 14. Patient 14 ordinarily, but not necessarily, will be a human. Therapy system 10 includes IMD 16, which is coupled to leads 18, 20, and 22, and programmer 24. IMD 16 may be, for example, an implantable pacemaker, cardioverter, and/or defibrillator that provides electrical signals to heart 12 via electrodes coupled to one or more of leads 18, 20, and 22. Each of leads 18, 20 and 22 may carry one or a set of electrodes. The electrode may extend about the circumference of each of leads 18, 20, and 22 and is positioned at a respective axial position along the length of each of the lead 18, 20, and 22.

Leads 18, 20, 22 extend into the heart 12 of patient 14 to sense electrical activity of heart 12 and/or deliver a therapy that may be in the form electrical stimulation to heart 12. Collectively, the sensing or therapy delivery will be referred to herein as a medical function. In the example shown in FIG. 1, right ventricular lead 18 extends through one or more veins (not shown), the superior vena cava (not shown), and right atrium 26, and into right ventricle 28. Left ventricular coronary sinus lead 20 extends through one or more veins, the vena cava, right atrium 26, and into the coronary sinus 30 to a region adjacent to the free wall of left ventricle 32 of heart 12. In alternative embodiments, the LV lead 20 may also be introduced into the left ventricle through the septal wall. Right atrial lead 22 extends through one or more veins and the vena cava, and into the right atrium 26 of heart 12.

IMD 16 may sense electrical signals attendant to the depolarization and repolarization of heart 12 via electrodes (not shown in FIG. 1) coupled to at least one of the leads 18, 20, 22. In some examples, IMD 16 provides pacing pulses to heart 12 based on the electrical signals sensed within heart 12. The configurations of electrodes used by IMD 16 for sensing and pacing may be unipolar or bipolar. IMD 16 may also provide defibrillation therapy and/or cardioversion therapy via electrodes located on at least one of the leads 18, 20, 22. IMD 16 may detect arrhythmia of heart 12, such as fibrillation of ventricles 28 and 32, and deliver defibrillation therapy to heart 12 in the form of electrical pulses. In some examples, IMD 16 may be programmed to deliver a progression of therapies, e.g., pulses with increasing energy levels, until a fibrillation of heart 12 is stopped. IMD 16 detects fibrillation employing one or more fibrillation detection techniques known in the art.

In some examples, programmer 24 may be a handheld computing device or a computer workstation. Programmer 24 may include a user interface that receives input from a user. The user interface may include, for example, a keypad and a display, which may for example, be a cathode ray tube (CRT) display, a liquid crystal display (LCD) or light emitting diode (LED) display. The keypad may take the form of an alphanumeric keypad or a reduced set of keys associated with particular functions. Programmer 24 can additionally or alternatively include a peripheral pointing device, such as a mouse, via which a user may interact with the user interface. In some embodiments, a display of programmer 24 may include a touch screen display, and a user may interact with programmer 24 via the display.

A user, such as a physician, technician, or other clinician, may interact with programmer 24 to communicate with IMD 16. For example, the user may interact with programmer 24 to retrieve physiological or diagnostic information from IMD 16. A user may also interact with programmer 24 to program IMD 16, e.g., select values for operational parameters of the IMD.

For example, the user may use programmer 24 to retrieve information from IMD 16 regarding the rhythm of heart 12, trends therein over time, or tachyarrhythmia episodes. As another example, the user may use programmer 24 to retrieve information from IMD 16 regarding other sensed physiological parameters of patient 14, such as intracardiac or intravascular pressure, activity, posture, respiration, or thoracic impedance. As another example, the user may use programmer 24 to retrieve information from IMD 16 regarding the performance or integrity of IMD 16 or other components of system 10, such as leads 18, 20, and 22, or a power source of IMD 16.

The user may use programmer 24 to program a therapy progression, select electrodes used to deliver defibrillation shocks, select waveforms for the defibrillation shock, or select or configure a fibrillation detection algorithm for IMD 16. The user may also use programmer 24 to program aspects of other therapies provided by IMD 16, such as cardioversion or pacing therapies. In some examples, the user may activate certain features of IMD 16 by entering a single command via programmer 24, such as depression of a single key or combination of keys of a keypad or a single point-and-select action with a pointing device.

IMD 16 and programmer 24 may communicate via wireless communication using any techniques known in the art. Examples of communication techniques may include, for example, low frequency or radiofrequency (RF) telemetry, but other techniques are also contemplated. In some examples, programmer 24 may include a programming head that may be placed proximate to the patient's body near the IMD 16 implant site in order to improve the quality or security of communication between IMD 16 and programmer 24.

Figure 2:
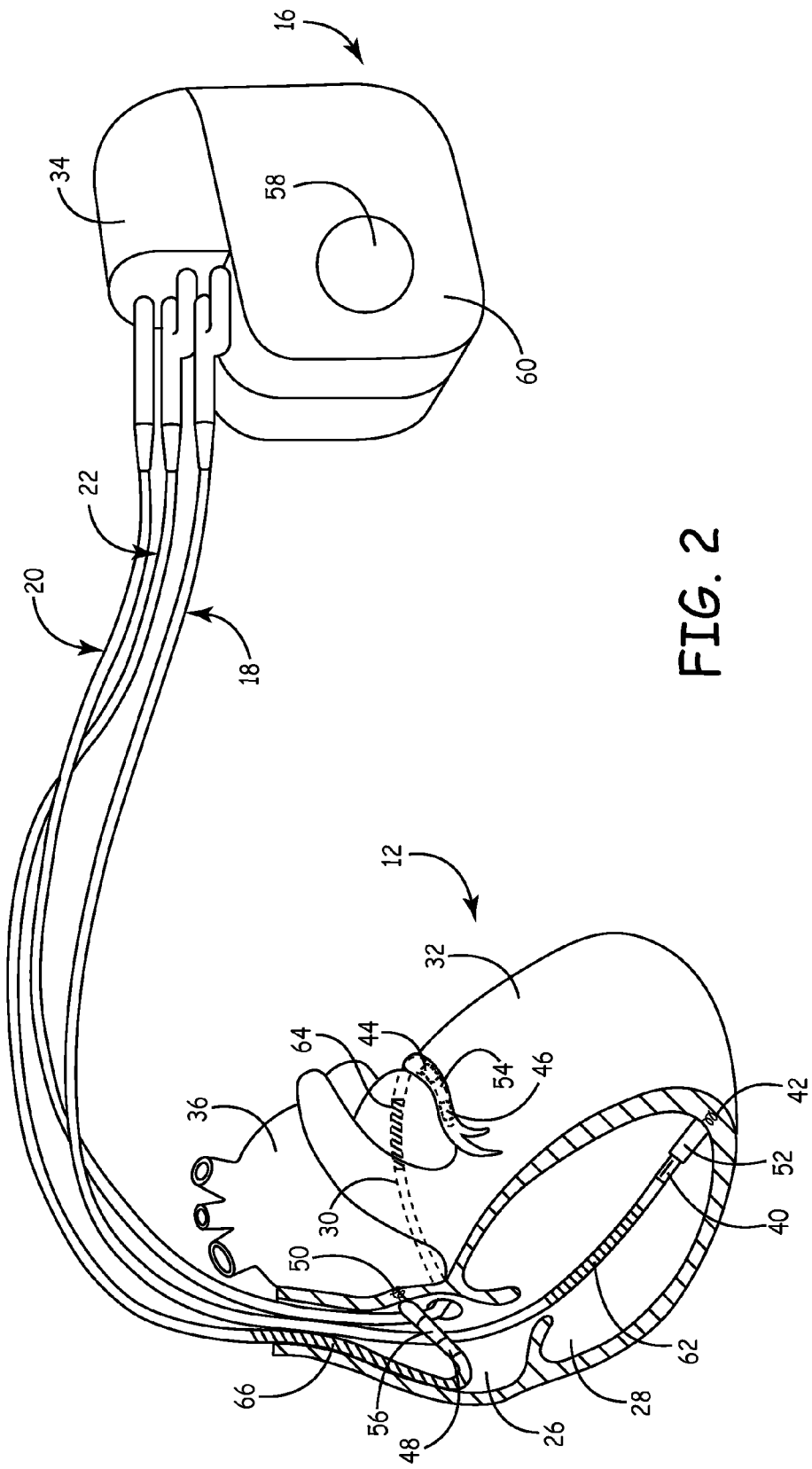
FIG. 2 is a conceptual diagram illustrating an implantable medical device and leads of therapy system in greater detail.

FIG. 2 is a conceptual diagram illustrating IMD 16 and leads 18, 20, 22 of therapy system 10 in greater detail. Leads 18, 20, 22 may be electrically coupled to a stimulation generator, a sensing module, or other modules of IMD 16 via connector block 34. In some examples, proximal ends of leads 18, 20, 22 may include electrical contacts that electrically couple to respective electrical contacts within connector block 34. In addition, in some examples, leads 18, 20, 22 may be mechanically coupled to connector block 34 with the aid of set screws, connection pins or another suitable mechanical coupling mechanism.

Each of the leads 18, 20, 22 includes an elongated insulative lead body, which may carry a number of concentric coiled conductors separated from one another by tubular insulative sheaths. In the illustrated example, a pressure sensor 38 and bipolar electrodes 40 and 42 are located proximate to a distal end of lead 18. In addition, bipolar electrodes 44 and 46 are located proximate to a distal end of lead 20 and bipolar electrodes 48 and 50 are located proximate to a distal end of lead 22. In FIG. 2, pressure sensor 38 is disposed in right ventricle 28. Pressure sensor 30 may respond to an absolute pressure inside right ventricle 28, and may be, for example, a capacitive or piezoelectric absolute pressure sensor. In other examples, pressure sensor 30 may be positioned within other regions of heart 12 and may monitor pressure within one or more of the other regions of heart 12, or may be positioned elsewhere within or proximate to the cardiovascular system of patient 14 to monitor cardiovascular pressure associated with mechanical contraction of the heart.

Among the electrodes, some of the electrodes may be provided in the form of coiled electrodes that form a helix, while other electrodes may be provided in different forms. Further, some of the electrodes may be provided in the form of tubular electrode sub-assemblies that can be pre-fabricated and positioned over the body of leads 18, 20, 22, where they are attached and where electrical connections with conductive elements within the leads 18, 20, 22 can be made. For example, electrodes 40, 44 and 48 may take the form of ring electrodes, and electrodes 42, 46 and 50 may take the form of extendable helix tip electrodes mounted retractably within insulative electrode heads 52, 54 and 56, respectively. Each of the electrodes 40, 42, 44, 46, 48 and 50 may be electrically coupled to a respective one of the coiled conductors within the lead body of its associated lead 18, 20, 22, and thereby coupled to respective ones of the electrical contacts on the proximal end of leads 18, 20 and 22.

Electrodes 40, 42, 44, 46, 48 and 50 may sense electrical signals attendant to the depolarization and repolarization of heart 12. The electrical signals are conducted to IMD 16 via the respective leads 18, 20, 22. In some examples, IMD 16 also delivers pacing pulses via electrodes 40, 42, 44, 46, 48 and 50 to cause depolarization of cardiac tissue of heart 12. In some examples, as illustrated in FIG. 2, IMD 16 includes one or more housing electrodes, such as housing electrode 58, which may be formed integrally with an outer surface of hermetically-sealed housing 60 of IMD 16 or otherwise coupled to housing 60. In some examples, housing electrode 58 is defined by an uninsulated portion of an outward facing portion of housing 60 of IMD 16. Other division between insulated and uninsulated portions of housing 60 may be employed to define one or more housing electrodes. In some examples, housing electrode 58 comprises substantially all of housing 60. Any of the electrodes 40, 42, 44, 46, 48 and 50 may be used for unipolar sensing or pacing in combination with housing electrode 58. As is known in the art, housing 60 may enclose a stimulation generator that generates cardiac pacing pulses and defibrillation or cardioversion shocks, as well as a sensing module for monitoring the patient's heart rhythm.

Leads 18, 20, 22 also include elongated electrodes 62, 64, 66, respectively, which may take the form of a coil. IMD 16 may deliver defibrillation shocks to heart 12 via any combination of elongated electrodes 62, 64, 66, and housing electrode 58. Electrodes 58, 62, 64, 66 may also be used to deliver cardioversion pulses to heart 12. Electrodes 62, 64, 66 may be fabricated from any suitable electrically conductive material, such as, but not limited to, platinum, platinum alloy or other materials known to be usable in implantable defibrillation electrodes.

Pressure sensor 38 may be coupled to one or more coiled conductors within lead 18. In FIG. 2, pressure sensor 38 is located more distally on lead 18 than elongated electrode 62. In other examples, pressure sensor 38 may be positioned more proximally than elongated electrode 62, rather than distal to electrode 62. Further, pressure sensor 38 may be coupled to another one of the leads 20, 22 in other examples, or to a lead other than leads 18, 20, 22 carrying stimulation and sense electrodes.

The configuration of therapy system 10 illustrated in FIGS. 1 and 2 is merely one example. In other examples, a therapy system may include epicardial leads and/or patch electrodes instead of or in addition to the transvenous leads 18, 20, 22 illustrated in FIG. 1. Further, IMD 16 need not be implanted within patient 14. In examples in which IMD 16 is not implanted in patient 14, IMD 16 may deliver defibrillation shocks and other therapies to heart 12 via percutaneous leads that extend through the skin of patient 14 to a variety of positions within or outside of heart 12.

In other examples of therapy systems that provide electrical stimulation therapy to heart 12, a therapy system may include any suitable number of leads coupled to IMD 16, and each of the leads may extend to any location within or proximate to heart 12. For example, other examples of therapy systems may include three transvenous leads located as illustrated in FIGS. 1 and 2, and an additional lead located within or proximate to left atrium 33. Other examples of therapy systems may include a single lead that extends from IMD 16 into right atrium 26 or right ventricle 28, or two leads that extend into a respective one of the right ventricle 26 and right atrium 28. An example of this type of therapy system is shown in FIG. 3.

Figure 3:
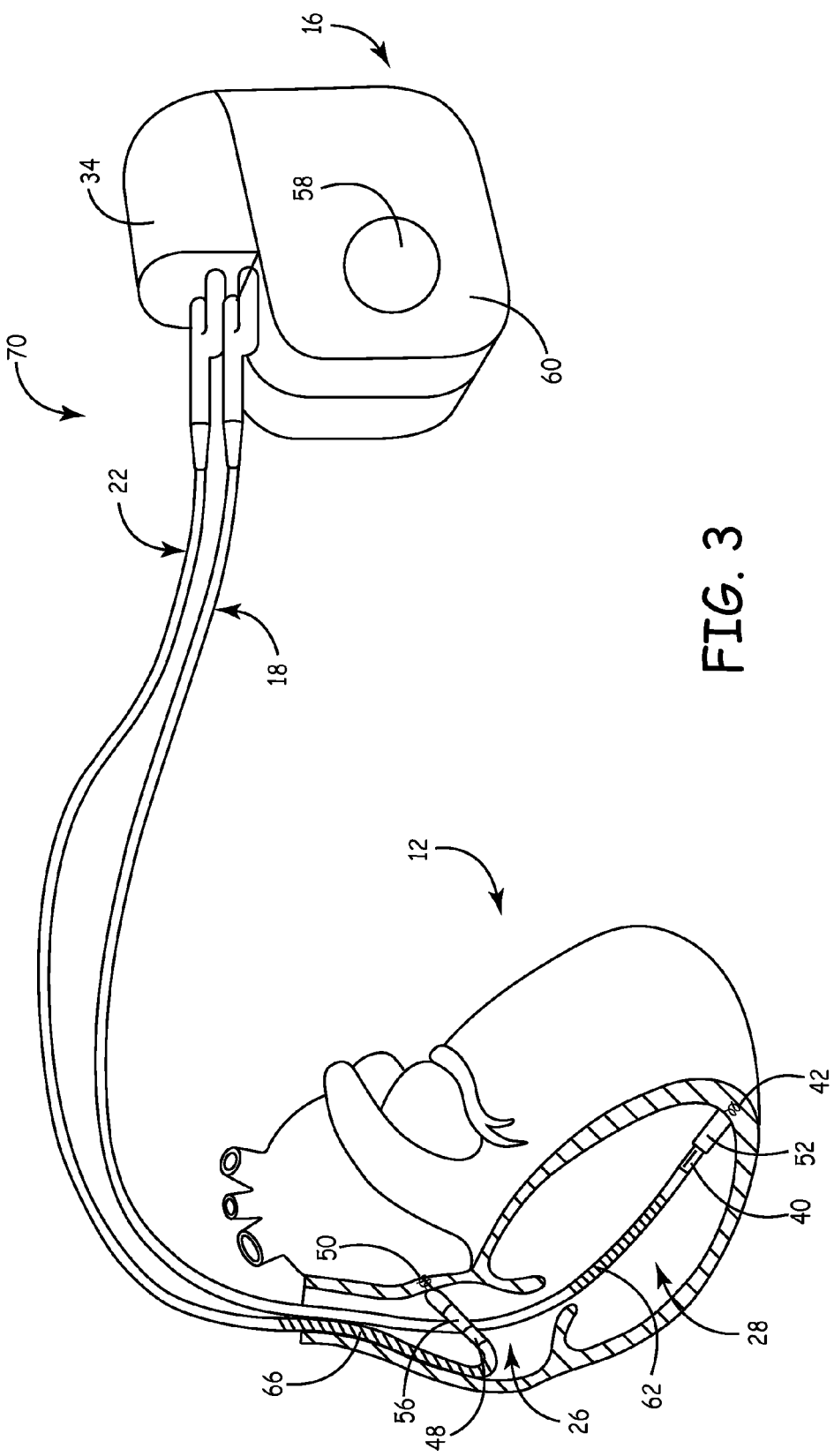
FIG. 3 is a conceptual diagram illustrating another exemplary therapy system.

FIG. 3 is a conceptual diagram illustrating another example of therapy system 70, which is similar to therapy system 10 of FIGS. 1-2, but includes two leads 18, 22, rather than three leads. Leads 18, 22 are implanted within right ventricle 28 and right atrium 26, respectively. Therapy system 70 shown in FIG. 3 may be useful for providing defibrillation and pacing pulses to heart 12.

Figure 4:
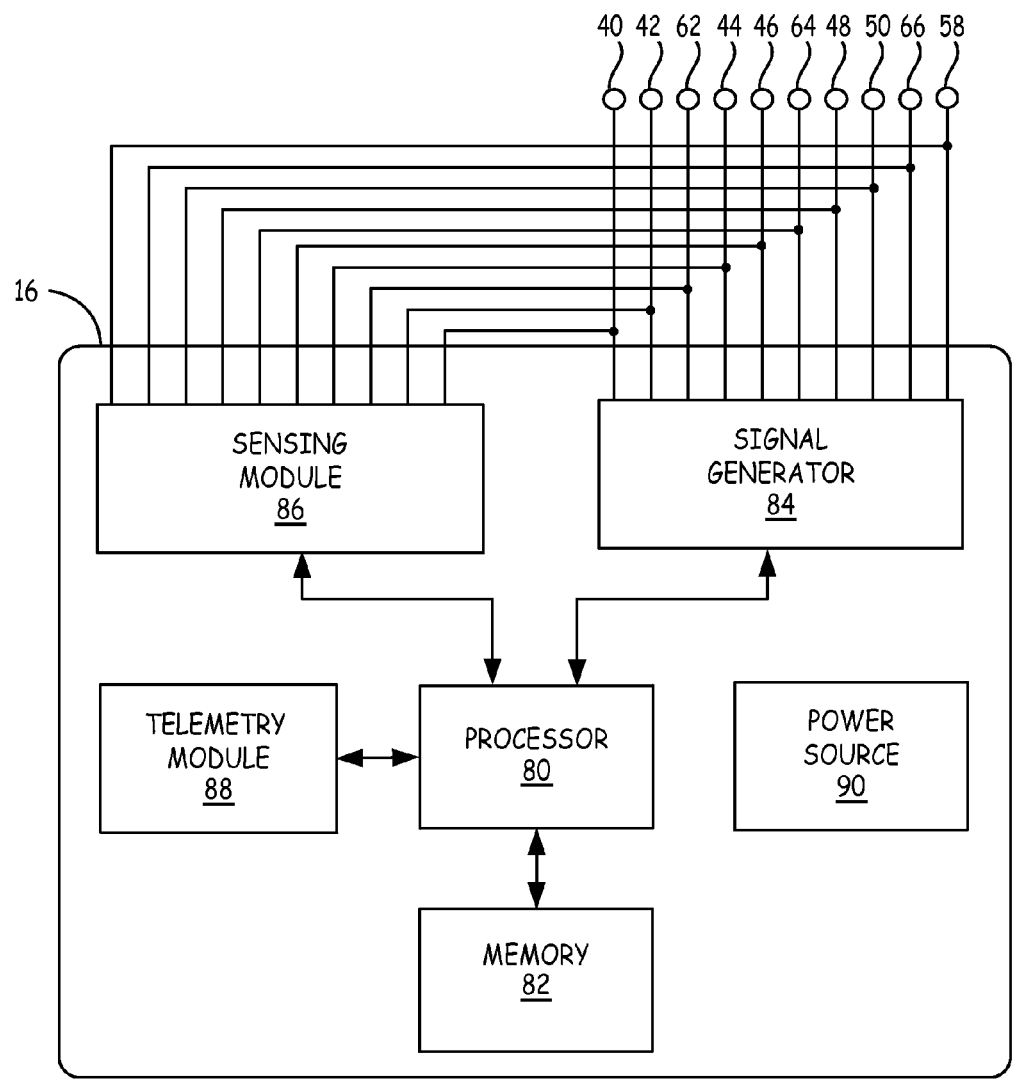
FIG. 4 is a functional block diagram of one example configuration of an implantable medical device.

FIG. 4 is a functional block diagram of one example configuration of IMD 16, which includes processor 80, memory 82, stimulation generator 84, sensing module 86, telemetry module 88, and power source 90. Memory 82 includes computer-readable instructions that, when executed by processor 80, cause IMD 16 and processor 80 to perform various functions attributed to IMD 16 and processor 80 herein. Memory 82 may include any volatile, non-volatile, magnetic, optical, or electrical media, such as a random access memory (RAM), read-only memory (ROM), non-volatile RAM (NVRAM), electrically-erasable programmable ROM (EEPROM), flash memory, or any other digital media.

Processor 80 controls stimulation generator 84 to deliver stimulation therapy to heart 12 according to a selected one or more of therapy programs, which may be stored in memory 82. Specifically, processor 44 may control stimulation generator 84 to deliver electrical pulses with the amplitudes, pulse widths, frequency, or electrode polarities specified by the selected one or more therapy programs.

Stimulation generator 84 is electrically coupled to electrodes 40, 42, 44, 46, 48, 50, 58, 62, 64, and 66, e.g., via conductors of the respective lead 18, 20, 22, or, in the case of housing electrode 58, via an electrical conductor disposed within housing 60 of IMD 16. Stimulation generator 84 is configured to generate and deliver electrical stimulation therapy to heart 12. For example, stimulation generator 84 may deliver defibrillation shocks to heart 12 via at least two electrodes 58, 62, 64, 66. Stimulation generator 84 may deliver pacing pulses via ring electrodes 40, 44, 48 coupled to leads 18, 20, and 22, respectively, and/or helical electrodes 42, 46, and 50 of leads 18, 20, and 22, respectively. In some examples, stimulation generator 84 delivers pacing, cardioversion, or defibrillation stimulation in the form of electrical pulses. In other examples, stimulation generator may deliver one or more of these types of stimulation in the form of other signals, such as sine waves, square waves, or other substantially continuous time signals.

Stimulation generator 84 may include a switch module and processor 80 may use the switch module to select, e.g., via a data/address bus, which of the available electrodes are used to deliver defibrillation shocks or pacing pulses. The switch module may include a switch array, switch matrix, multiplexer, or any other type of switching device suitable to selectively couple stimulation energy to selected electrodes.

Sensing module 86 monitors signals from at least one of electrodes 40, 42, 44, 46, 48, 50, 58, 62, 64 or 66 in order to monitor electrical activity of heart 12, e.g., via electrocardiogram (ECG) signals. Sensing module 86 may also include a switch module to select which of the available electrodes are used to sense the heart activity. In some examples, processor 80 may select the electrodes that function as sense electrodes via the switch module within sensing module 86, e.g., by providing signals via a data/address bus. In some examples, sensing module 86 includes one or more sensing channels, each of which may comprise an amplifier. In response to the signals from processor 80, the switch module of within sensing module 86 may couple the outputs from the selected electrodes to one of the sensing channels.

In some examples, one channel of sensing module 86 may include an R-wave amplifier that receives signals from electrodes 40 and 42, which are used for pacing and sensing in right ventricle 28 of heart 12. Another channel may include another R-wave amplifier that receives signals from electrodes 44 and 46, which are used for pacing and sensing proximate to left ventricle 32 of heart 12. In some examples, the R-wave amplifiers may take the form of an automatic gain controlled amplifier that provides an adjustable sensing threshold as a function of the measured R-wave amplitude of the heart rhythm.

In addition, in some examples, one channel of sensing module 86 may include a P-wave amplifier that receives signals from electrodes 48 and 50, which are used for pacing and sensing in right atrium 26 of heart 12. In some examples, the P-wave amplifier may take the form of an automatic gain controlled amplifier that provides an adjustable sensing threshold as a function of the measured P-wave amplitude of the heart rhythm. Examples of R-wave and P-wave amplifiers are described in U.S. Pat. No. 5,117,824 to Keimel et al., which issued on Jun. 2, 1992 and is entitled, "Apparatus for Monitoring Electrical Physiologic Signals," and is incorporated herein by reference in its entirety. Other amplifiers may also be used. Furthermore, in some examples, one or more of the sensing channels of sensing module 86 may be selectively coupled to housing electrode 58, or elongated electrodes 62, 64, or 66, with or instead of one or more of electrodes 40, 42, 44, 46, 48 or 50, e.g., for unipolar sensing of R-waves or P-waves in any of chambers 26, 28, or 32 of heart 12.

In some examples, sensing module 86 includes a channel that comprises an amplifier with a relatively wider pass band than the R-wave or P-wave amplifiers. Signals from the selected sensing electrodes that are selected for coupling to this wide-band amplifier may be provided to a multiplexer, and thereafter converted to multi-bit digital signals by an analog-to-digital converter for storage in memory 82 as an electrogram (EGM). In some examples, the storage of such EGMs in memory 82 may be under the control of a direct memory access circuit. Processor 80 may employ digital signal analysis techniques to characterize the digitized signals stored in memory 82 to detect and classify the patient's heart rhythm from the electrical signals. Processor 80 may detect and classify the heart rhythm of patient 14 by employing any of the numerous signal processing methodologies known in the art.

Telemetry module 88 includes any suitable hardware, firmware, software or any combination thereof for communicating with another device, such as programmer 24 (FIG. 1). Under the control of processor 80, telemetry module 88 may receive downlink telemetry from and send uplink telemetry to programmer 24 with the aid of an antenna, which may be internal and/or external. Processor 80 may provide the data to be uplinked to programmer 24 and the control signals for the telemetry circuit within telemetry module 88, e.g., via an address/data bus. In some examples, telemetry module 88 may provide received data to processor 80 via a multiplexer.

In some examples, processor 80 may transmit atrial and ventricular heart signals (e.g., electrocardiogram signals) produced by atrial and ventricular sense amp circuits within sensing module 86 to programmer 24. Programmer 24 may interrogate IMD 16 to receive the heart signals. Processor 80 may store heart signals within memory 82, and retrieve stored heart signals from memory 82.

The various components of IMD 16 are coupled to power source 90, which may include a rechargeable or non-rechargeable battery. A non-rechargeable battery may be selected to last for several years, while a rechargeable battery may be inductively charged from an external device, e.g., on a daily or weekly basis.

As depicted in FIGS. 1-4, one or more of leads 18, 20, 22 are electrically coupled to medical device 16 that is implanted at a medically suitable location in patient 10 during use. The leads 18, 20, 22 extend from medical device 16, where the proximal ends are connected, to another suitable location in the patient where the distal end portions are adjacent to the desired organ/tissue of patient 10.

In constructing the bodies of leads 18, 20, 22, various considerations are typically taken into account to maintain the integrity of the implanted leads. One such consideration is the continuous flexing of the leads 18, 20, 22 due to the beating of the heart. Other considerations are the stresses applied to the lead body during an implantation or lead repositioning procedure. Movements by the patient can cause the route traversed by the lead body to be constricted or otherwise altered causing stresses on the lead body. At times, the lead bodies can be slightly damaged because of improper handling, and the slight damage can progress in the body environment resulting in a fracture to the lead conductor and/or a breach of the insulation. The effects of lead body degradation can progress from an intermittent manifestation to a more continuous effect and this may occur gradually over time or instantaneously. In extreme cases, insulation of one or more of the electrical conductors can be breached, causing the conductors to contact one another or body fluids resulting in a low impedance or short circuit. In other cases, a lead conductor can fracture and exhibit an intermittent or continuous/static open circuit resulting in intermittent or continuous high impedance as well as noise.

These and other such lead issues affecting the conductive pathway, which is comprised of one or both the conductor and insulation, and resulting in partial or complete short or open circuits, for example, can be referred to, for simplicity, as "lead-related conditions." In other words, the lead-related condition may relate to a lead hardware degradation that has crossed a material or behavioral threshold that increases the probability of undesirable functionality leading to an adverse system event. Undesirable functionality may be hardware, firmware, or system functionality that leads to inappropriate decisions.

In the case of cardiac leads, the ability to sense cardiac activity conditions accurately through a lead can be impaired by these lead-related conditions. Complete lead breakage impedes any sensing functions while lead conductor fractures or intermittent contact can demonstrate electrical noise that interferes with accurate sensing. During cardiac pacing or defibrillation therapy, lead-related conditions can reduce the effectiveness of a pacing or defibrillation therapy below that sufficient to pace or defibrillate the heart. The lead-related conditions may also contribute to systemic decisions that may lead to inappropriate therapy delivery unless the conditions are recognized and managed.

With the above brief overview in mind, the inventors of the present disclosure have recognized that conventional scheduled detection and measurement techniques may fail to recognize the lead-related condition immediately or on a scheduled basis. Conventional techniques may also fail to recognize leading indicators that would provide an opportunity to support continued sensing and therapy delivery operations and principles of fault tolerant system designs. As such, methods and devices of the present disclosure are directed to promoting early detection of these lead-related conditions and dynamically adapting the lead for continued functionality in the presence of the lead-related condition.

Figure 5:
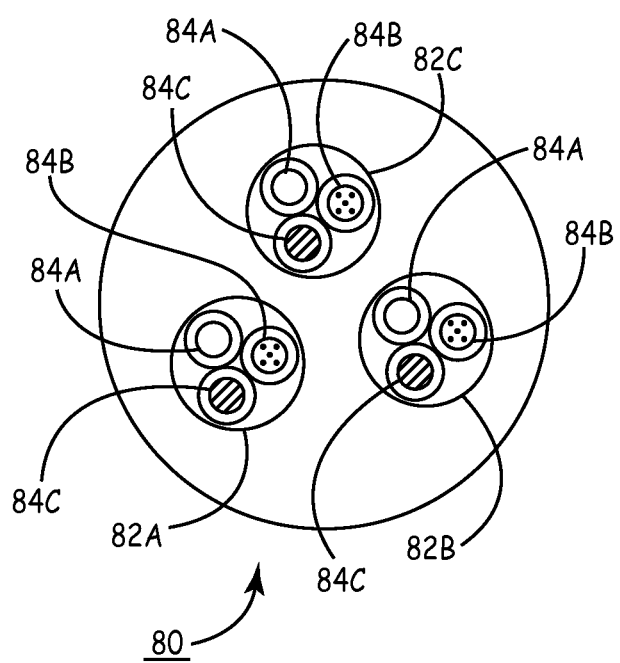
FIG. 5 is a functional block diagram illustrating the interrelation of an exemplary signal stability module in conjunction with a lead in accordance with an embodiment of the present disclosure.

FIG. 5 illustrates a section view of a lead body 80 according to an embodiment of the disclosure. The lead body 80 may correspond to any of the aforementioned leads 18, 20, and 22. The depicted view shows the lead body 80 having a plurality of lumens 82A, 82B, and 82C (collectively "82") with each lumen having a plurality of insulated conductors 84A, 84B, and 84C (collectively "84"). The insulation around each given conductors 84 isolates the given conductor from other conductors in the same lumen. In one embodiment, two or more of the insulated conductors 84 in each lumen 82 may be coupled to a single electrode. As an illustration, the three insulated conductors in lumen 82A may each be coupled to electrode 62 in lead 18, for example. In another embodiment, one of the three insulated conductors 84 in each of lumens 82A, 82B, and 82C may be coupled to the same electrode. Again, to illustrate, one insulated conductor 84 in each of the lumens 82A, 82B and 82C may be coupled to electrode 62 of lead 18, for example. For construction of the insulated conductors, different insulation and conductive materials may be used for each set of insulated conductors that is coupled to a single electrode. Utilizing different materials will enable optimization of lead body 80 for different longevity goals, different sensing goals, and different pacing goals.

For example, the materials may be selected such that insulated conductor 84A functions as the initial primary sense path and is optimized for sensing and longevity. Insulated conductor 84B may be optimized to enable sub-optimal pacing while promoting an increased longevity in relation to the insulated conductor 84A. As such, insulated conductor 84B supports graceful degradation in the event of a lead-related condition. Even further, insulated conductor 84C may provide a third electrical pathway that also serves as a fault tolerance loop return for future lead test patterns.

Coupling multiple conductors to a single electrode provides redundancy in the event of a lead-related condition associated with one of the insulated conductors 84 and enables dynamic reconfiguration of the system in response to a detected lead-related condition. The system may identify one of the insulated conductors that is coupled to each given electrode as the primary conductor and thereby establish a primary electrical pathway via the given conductor. The primary conductor may be the initial conductor that is chosen during implant of the system and the sensing or therapy delivery functions of the system may be optimized for the selected conductor. The other(s) of the insulated conductors may function as redundant pathways. As such, upon detecting a lead-related condition associated with the chosen conductor, the present disclosure facilitates determination of a suitable alternative conductor from the redundant insulated conductors to enable dynamic reconfiguration of the electrical pathway for sustained sensing and therapy delivery functions.

By coupling multiple insulated conductors in the same or different lumens to a single electrode, a more robust system that provides increased longevity can be attained. This is because the various physical stresses acting on the lead will impact each set of insulated conductors in the different lumens differently.

FIGS. 6-11 describe aspects permitting the dynamic reconfiguration of multiple conductors in a lead in accordance with the embodiments of the disclosure.

Figure 6:
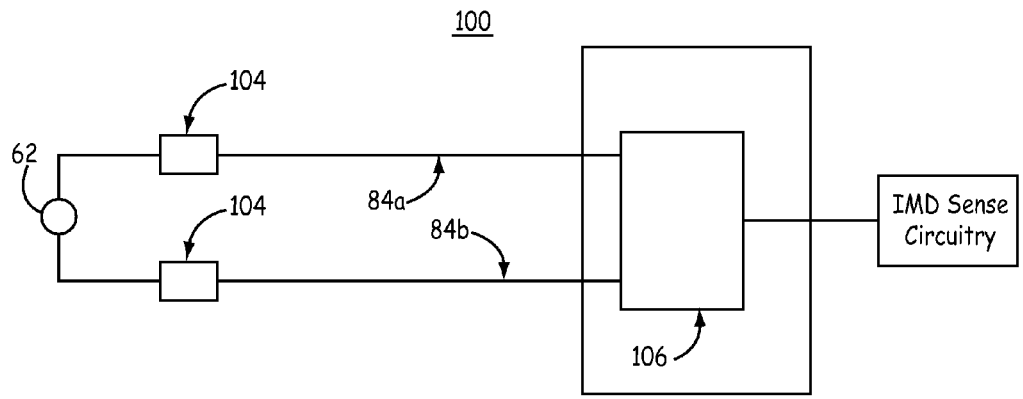
FIG. 6 depicts a functional block diagram illustrating several exemplary components of an embodiment of the signal stability module.

Turning first to FIG. 6, a block diagram is shown illustrating in further detail a medical sub-system 100 in accordance with the disclosure. Medical sub-system 100 comprises a lead such as lead 18, containment modules 104 and a sense path arbiter 106.

Consistent with the exemplary lead body 80, lead 18 comprises two or more conductors 84. Each of the conductors 84 is coupled to a respective one of the containment modules 104. The conductors 84 comprise an electrically conductive material and define a primary electrical pathway and a secondary electrical pathway. In embodiments in which lead 18 includes more than two conductors coupled to each electrode, the additional conductors may define alternate or secondary electrical pathways. The designation of the primary electrical pathway and secondary electrical pathway(s) is merely intended to indicate that in the absence of a lead-related condition, one of the conductors is designated as the default electrical pathway. The secondary conductors may provide an alternate pathway in response to detection of a lead-related condition. Thus, in the embodiment, lead 18 further comprises an electrode such as electrode 62 that is coupled at the distal end as illustrated in FIG. 2.

The containment module 104 is coupled in series to the conductor 84 such as by connecting a first terminal of the containment module 104 to the electrode 62 and a second terminal to a distal end of conductor 84. Alternatively, containment module 104 may be disposed along the length of conductor 84 either serially or in parallel. The containment module 104 may be biased in such a way that physiological signals are propagated from the distal end to the proximal end of the conductor without any signal loss. The containment module 104 may also be biased to inhibit propagation of signals from the proximal end of one conductor to the distal end of the conductor and/or the electrode or sensing element at the distal end. In one embodiment, the containment module 104 may be implemented as a filter that contains (or prevents propagation of) a first signal transmitted from electrode 62 while permitting a second signal to propagate through to the proximal end of conductor 84. As an example, the containment will prevent propagation of noise signals while permitting depolarization signals to be propagated through to the proximal lead end. In another embodiment, containment module 104 may be implemented as a diode that will permit electrical signal propagation in only one direction. As such, the containment module 104 will prevent interference arising from signals propagated through a conductor on lead 18 exhibiting a lead-related condition. That is to say, the functionality of the containment module 104 prevents interference on the sense path, defined by a primary conductor, when dynamic reconfiguration has been performed due to a lead-related condition associated with another of the conductors in lead 18.

Sense path arbiter 106 may be disposed at a proximal end of lead 18 and coupled to conductor 84. In other words, sense path arbiter 106 may be integrated within lead 18. In another embodiment, sense path arbiter 106 is coupled to the proximal end of lead 18. The sense path arbiter 106 will function to monitor electrical signals propagated through conductors 84. Signal processing of the received signals may be performed to detect a discontinuity that may indicate the presence of a lead-related condition. The discontinuity may be a transient discontinuity or a static discontinuity, either of which will provide an indication of the level of degradation of the lead 18.

The sense path arbiter 106 may employ recognition criteria that facilitate real-time or instantaneous recognition of a lead-related condition. Such criteria may be utilized to monitor the conductors 84 to detect the occurrence of the lead-related condition. As an example, the criteria employed may include duration and frequency of a signal propagated through lead 18. In the event that the integrity of one of conductors 84 is compromised, the pattern (as manifested in the criteria) of electrical signals transmitted through that conductor is distinguishable from the pattern of electrical signals transmitted through an intact conductor. The criteria may be continuously updated based on processing results of a received signal to create a feedback loop that enables self-tuning or learning of algorithms used for detecting the lead-related condition.

The sense path arbiter 106 monitors the conductors 84 to detect and receive transients, analyze the received transients, and determine whether a lead-related condition is present based on the results of the analysis. In response to detecting a lead-related condition on the primary conductor, sense path arbiter 106 reconfigures the conductors associated with the electrode for transmission of signals from the electrode to an IMD coupled to the lead 18. The reconfiguration involves determining which of the secondary conductors will provide optimal performance to sustain sensing and/or therapy delivery functions of the lead or provide graceful degradation. The sense signal for the secondary conductor selected as optimal will then be configured electrically as the input signal to the sense circuits.

The transients may be classified in a variety of patterns, with each pattern indicating a specific lead-related condition, or a level of degradation of the conductor, or both. For example, two transient patterns may be defined: class A and class B. The class A transient pattern may be defined as one corresponding to a lead-related condition associated with an intermittent conductive path discontinuity. The pattern is one of discontinuities. The class B transient may be defined as one corresponding to a static or permanent conductive path discontinuity. For example, the class A transient pattern may be a non-physiological signal or signal discontinuity having a duration of about a hundred (100) nano-seconds to one (1) second and the class B transient may be a non-physiological signal or signal discontinuity having a duration greater than one (1) second. As such, detection of a signal having a duration between 100 nano-seconds to one second may result in the conductor being classified as exhibiting a class A lead-related condition while sensing of a signal having a duration greater than one second may result in that conductor being classified as exhibiting a class B lead-related condition. Class B patterns are often static, solid opens in a conductor.

The sense path arbiter 106 may employ a recognition window having adjustable time periods for monitoring electrical signals propagated through one of conductors 84. The recognition window may further be defined in terms of frequency or amplitude or any other desired electrical characteristic. In conjunction with the recognition window, the above-referenced recognition criteria may be used for analysis of the monitored signals. In one example, the analysis may comprise determining whether the received signals correspond to a predetermined pattern, such as one of class A or class B transient patterns. In response to detecting a class A pattern, the processing module 106 may be dynamically reconfigured to further characterize the nature of the lead-related condition. The reconfiguration may include expanding the length of the reconfiguration window or adjusting the interval between recognition windows to, for example, increase the frequency of the signal sampling. On the other hand, detection of a class B transient pattern may trigger a blanking response intended to prevent further use of the given conductor. In other words, the class B pattern may be associated with a lead-related condition that frustrates sensing or therapy delivery thereby rendering the conductor unsuitable for continued use. As such, by detecting and characterizing the nature of the lead-related condition, an accurate and meaningful tracking over time of the progression of a lead-related condition can be made.

In evaluating the multiple conductors 84, sense path arbiter 106 may perform the analysis of signals transmitted through the primary and secondary pathways simultaneously or sequentially for each conductor 84. The best path may be determined through comparison of the results obtained from the analysis. Those analysis results obtained by the sense path arbiter 106 are used in an arbitration scheme that selects one of the conductors 84 as the primary electrical pathway. The selected conductor 84 is used for transmission of sensed physiological signals to the IMD.

Figure 7:
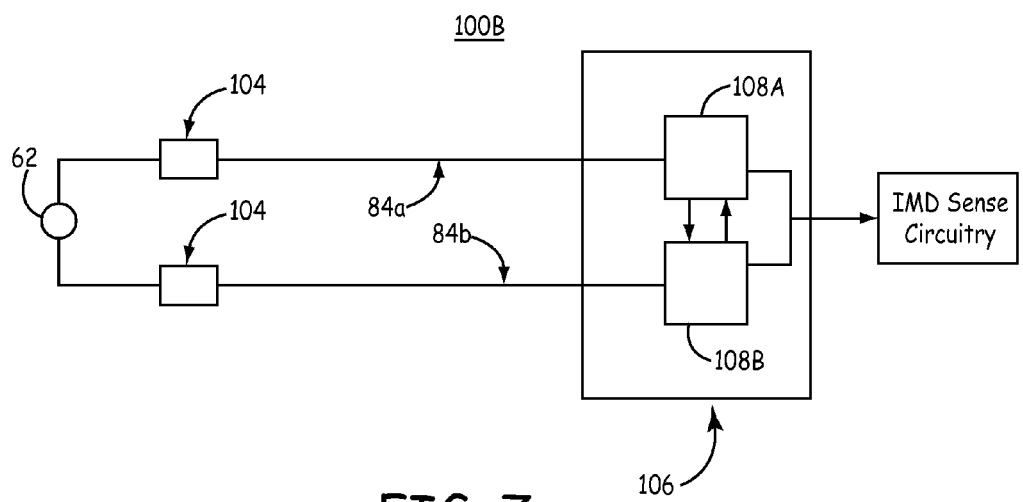
FIG. 7 depicts a functional block diagram illustrating several components of another embodiment of the signal stability module.

FIG. 7 illustrates a block diagram showing an alternative embodiment of the medical subs-system 100B. In the alternative embodiment, the sense path arbiter 106 includes a principal arbiter circuit 108A and an associate arbiter circuit 108B. The principal and associate arbiter circuits 108A and 108B will monitor the primary and secondary conductors 84, respectively, to detect transients, analyze the received transients, and determine whether a lead-related condition is present based on the results of the analysis. Further, the principal and associate arbiter circuits 108A and 108B will collaborate to arbitrate between the primary and secondary conductors 84 to select one of the conductors for transmission of signals from the electrode to an IMD coupled to the lead 18. Hence, in the response to detecting a lead-related condition, the sense path arbiter 106 will arbitrate between the conductors 84 to determine which of the conductors 84 is most suitable for transmission of sensed signals to the IMD while mitigating the impact of the lead-related condition, for example.

Figure 8:
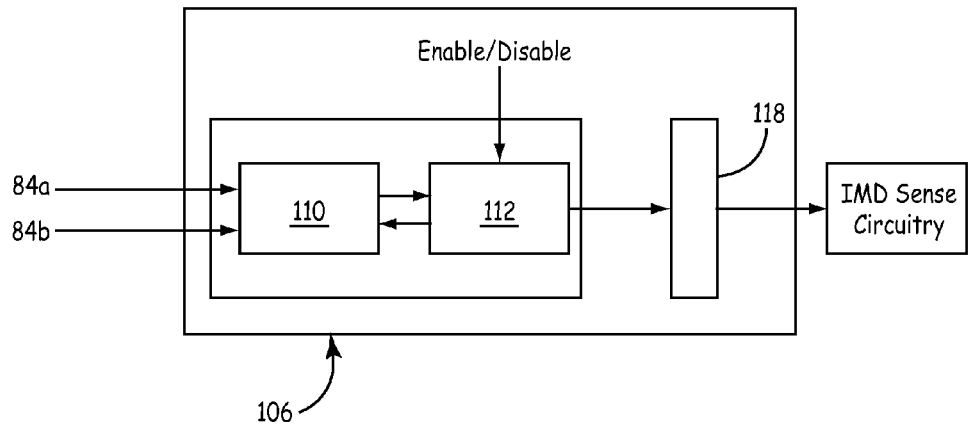
FIG. 8 depicts an illustrative circuit diagram of a signal stability module operable to detect state transitions.

FIG. 8 illustrates in more detail an embodiment of a sense path arbiter 106. The sense path arbiter 106, which may correspond to that of the medical sub-system 100 of FIG. 6 will generally receive a signal transmitted through conductors 84. As can be expected because of the coupling of multiple conductors 84 to one electrode or sensing element, the same signal may be propagated through each set of conductors 84 coupled to a common electrode or sensing element. In other embodiments, a single signal may be broken down into multiple signal packets, with the packets being distributed among the plurality of conductors with re-assembly of the signal being performed by the sense path arbiter 106 upon receipt. In either embodiment, the sense path arbiter 106 monitors the pathway defined by the plurality of conductors and this monitoring may be performed continuously and/or in real-time. As such, the disclosure facilitates immediate recognition of a lead-related condition that enables dynamic reconfiguration of the medical system functionalities for sustained sensing and therapy delivery.

In particular, the sense path arbiter 106 will receive signals propagated through the conductors 84 and analyze the signals to diagnose the presence of a lead-related condition. In so doing, one of the conductors 84 is selected as a function of the determination that it is the optimal electrical pathway for transmission of the signals.

Sense path arbiter 106 comprises a transient recognition element 110 and an arbitration element 112 that are coupled to the conductors 84. The transient recognition element 110 monitors for and receives electrical signals propagated through the conductors and analyzes the signals to detect leading indicators of a lead-related condition that may manifest as transients. The transient recognition element 110 will also identify the one of the plurality of conductors 84 from which the leading indicators originated.

The analysis performed by the transient recognition element 110 includes pattern analysis of a received signal to, for example, detect a deviation of the signal from a normal signal. A normal signal may be defined as one emanating from a sensed physiological event as opposed to a signal that may emanate from noise or other external influence as a result of a lead-related condition affecting the conductor. In other analytical operations, a template may be utilized that provides the reference "normal" signals and that template may be updated based on feedback pertaining to the accuracy of the initial template with regards to actual existence of a lead-related condition based on external data and/or confirmation via known lead integrity tests.

The arbitration element 112 performs an arbitration function—i.e., selection of one of the conductors 84 for coupling to the IMD sense circuitry. Arbitration is based on results of the analysis performed by the transient recognition element 110 indicating whether the primary conductor is exhibiting a lead-related condition. Based on the results, a given conductor 84 is selected as providing the most optimal electrical pathway in relation to the other conductors commonly-coupled to the electrode or sensing element. Through the arbitration process, the given conductor will be coupled to the IMD sense circuitry for transmission of signals from the electrode or sensing element.

Figure 9:
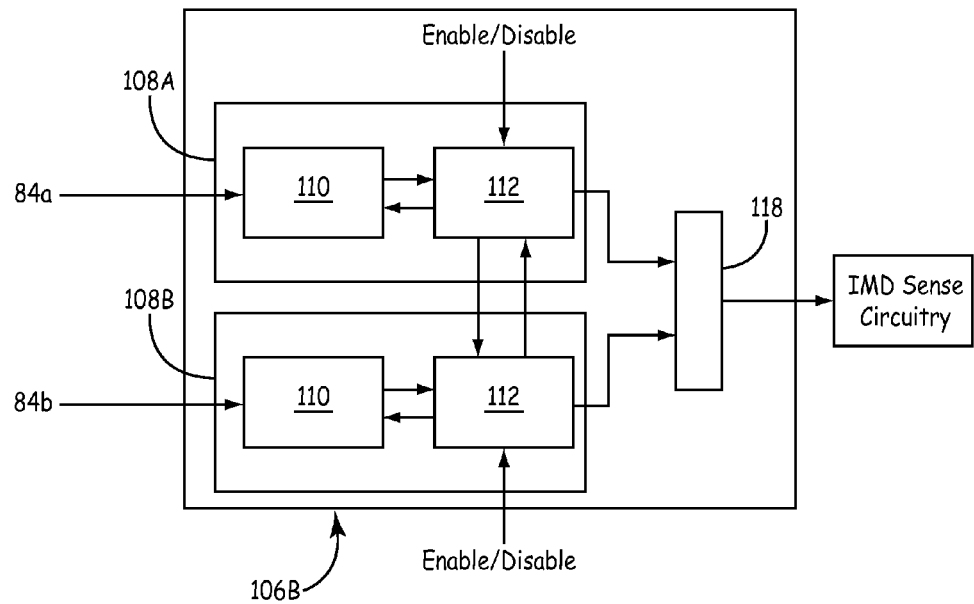
FIG. 9 depicts an alternative embodiment of a signal stability module in accordance with principles of this disclosure.

FIG. 9 illustrates an alternative embodiment of a sense path arbiter 106B. Similar to SPA 106, signals are sensed and propagated from the electrode or sensing element through the conductor and to the IMD sense circuitry that resides in the IMD. The components that are similar to those in FIG. 8 have been identified with identical reference designators and will not be discussed with respect to FIG. 9 for convenience. In the embodiment of FIG. 9, sense path arbiter 106B includes a set of transient recognition element 110 and arbitration element 112 for each individual conductor 84. The functionality of the transient recognition element 110 and arbitration element 112 in FIG. 9 is similar to that described with respect to FIG. 8. An advantage of including the transient recognition element 110 and arbitration element 112 as a set for each conductor 84 is that simultaneous analysis of the signals on the multiple conductors can be performed. This, of course, comes with the downside of increased overall real estate demand on the lead and thus these competing requirements must be balanced. Elements 110 and 112 may reside in the IMD in another embodiment however and not in the lead body itself.

The multiple sets of transient recognition element 110 and arbitration element 112 may function in a principal-associate relationship. Thus, one of the sets of transient recognition element 110 and arbitration element 112 may function as the principal and the other sets will derive control from the principal. The associates will provide acknowledgement of received control commands to the principal upon receipt of such commands. That is to say, the principal will direct the configuration/reconfiguration of the primary conductive pathway when determining which of the signals on the plurality of conductors is to be transmitted to the IMD. On the other hand, the associate only conducts the evaluation of the signals on the conductor 84 independently while performing all other configuration functions and data transmission at the request of the principal. As such, the principal can be viewed as the dominant element. For purposes of identification, each set of the transient recognition element 110 and arbitration element 112 will have an ID input line that denotes it as either the primary or associate. The ID input may be hardwired in one embodiment or connected to the IMD processing circuits in another embodiment to allow the IMD processor to determine the arbitration functionality.

The principle arbiter may request the secondary arbitor to provide a status of the conductor evaluated by the secondary recognition element. The secondary, in this case, will respond to the primary with secondary conductor status to assist the primary in decision making. The primary will then possess functional information about both the primary and the secondary conductive paths. The primary will either select the optimal conductive path as input to the sense circuits. The primary will direct the associate arbiter to configure its secondary path as input to the sense circuits if it concludes the secondary path is optimal compared to the primary path based on evaluation for both primary and secondary paths. The primary arbiter will disconnect the primary path and the associate arbiter will connect the secondary path as input to the sense circuit. The primary arbiter performs the sense path arbitration.

The multiple sets of transient recognition element 110 and arbitration element 112 may each be contained in separate (sense path arbiter 106) modules or they can all be included in a single module. Each of the sets of transient recognition element 110 and arbitration element 112 will communicate with each other to determine which conductor provides the optimal path for transmission of the sensed signals to the IMD sense circuit. The multiple sets of transient recognition element 110 and arbitration element 112 are coupled via bidirectional pathways to enable communication among each other of the results of processing and to facilitate reconfiguration in the event that the designation of the primary conductor needs to be changed.

The principal and associates will collectively transmit the signal propagated through their respective conductors to an output buffer 118 or will tri-state their outputs contingent on which sense path is transmitted. Each set of the transient recognition element 110 and arbitration element 112 will have a separate enable/disable input path to activate arbitration and reconfiguration functions.

Figure 10:
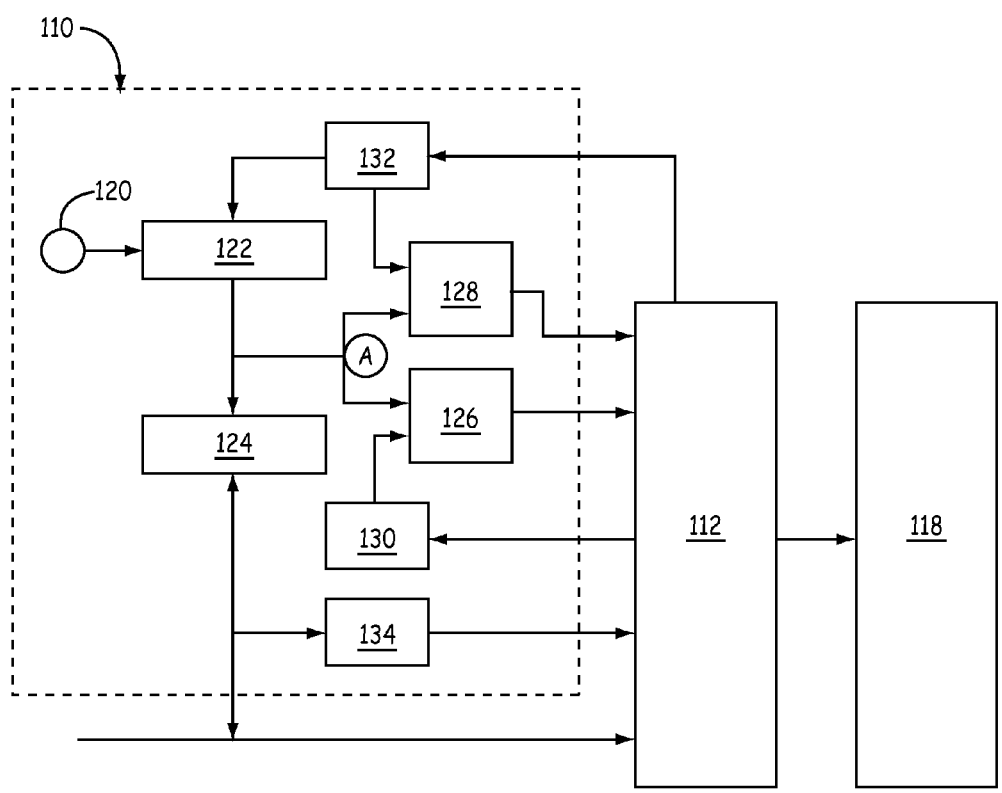
FIG. 10 illustrates a flow diagram of an illustrative method for detecting a lead-related condition.

FIG. 10 depicts a block diagram showing one embodiment of the sense path arbiter 106. The sense path arbiter 106 arbitrates the electrical pathways defined by the plurality of conductors 84 and determines which of the conductors will function as the primary electrical pathway with the rest of the conductors being designated as secondary pathways. The sense path arbiter 106 will couple the primary conductor to the IMD sense circuits and may also output the results of the analytical processing to the IMD. As described with reference to FIGS. 7 and 8, the sense path arbiter 106 includes transient recognition element 110 and arbitration element 112. The transient recognition element 110 manages the analysis of transmitted electrical signals on the plurality of conductors 84 for transient detection.

In one implementation, the transient recognition element 110 may include a limiter 124 that is coupled to a given one of the plurality of conductors 84. The given conductor 84 is also coupled to an arbitration element 112. The limiter 124 functions to monitor the given conductor 84 for an electrical signal. The limiter 124 isolates the sense signal from monitoring and recognition circuits while at the same time limiting current flow into the sense path. The limiter 124 may be a resistive component or may be an A/D converter digitizing the signal for further processing. Current regulator 122 manages the current and the upper voltage for node A in the event of a transient. Node A will always be a representation of a particular characteristic of the sensed signal and provides inputs to both recognition elements 126 and 128. Recognition elements 126 and 128 evaluate upper and lower limits for a particular characteristic of the sensed signal. A second of the terminals on recognition elements 126 and 128 is coupled to dynamic syncopated source 130 and 132, respectively. The dynamic syncopated sources 130 and 132 generate a reference signal under the direction of the arbitration element 112 and may comprise a voltage, current, or frequency reference. The reference signal may be a static input or a programmable variable-input reference signal and it establishes the sensitivity and threshold level to which received signals on conductor 84 are compared. The dynamic syncopated sources 130 and 132 will also output control settings for the current regulator 122 to manage power usage. That power may be provided from the IMD or from a power source 120.

The recognition elements 126 and 128 perform a processing function to detect a deviation of the received electrical signal from a threshold, which would indicate the presence of a lead-related condition. The recognition elements 126 and 128 will perform transient recognition by sensing a voltage deviation at node A between recognition elements 126 and 128. Recognition elements 126 and 128 may constitute a model that is sensitive to transient discontinuities in a lead conductive path and respond to the transient discontinuity with a voltage shift at node A while using negligible energy. In one example, recognition elements 126 and 128 may be voltage comparators, with each set to perform analysis of amplitude deviation of the received signal within a first and second range, respectively. The voltage at node A will be evaluated by recognition elements 126 and 128 and a result of the processing will indicate deviations from acceptable model parameters through state changes on the outputs of recognition elements 126 and 128. In the elementary example of the comparator, the recognition elements 126 and 128 will produce one of two outputs depending on whether the threshold reference signal is crossed. The threshold against which the monitored signal is compared may be established by the dynamic syncopated source 130 and 132 with the parameters being provided by the arbitration element 112. As such, a complete loop is established for the transient recognition element 110 that enables identification of early indicators of lead-related conditions and arbitration between multiple conductors to identify the optimum electrical pathway for dynamic reconfiguration of the conductive pathway. As such, leading indicators of a lead-related condition that may manifest as static and/or intermittent/dynamic conductive discontinuities can be detected to permit reconfiguration of the lead functionality.

It is also contemplated that one or more of the aforementioned reference signals may be provided to facilitate further characterization of the nature and type of lead-related condition being monitored. By way of an example that is not intended to be limiting, a first reference signal may be provided to evaluate the occurrence of a lead-related condition associated with a conductive discontinuity and a second reference signal may be provided for evaluations of the occurrence of a lead-related condition associated with an insulation breach. Other reference signals may be established to evaluate different types of lead-related conditions and their origins.

Moreover, while the recognition elements have been described in the context of an amplitude-related recognition criterion, other properties may be monitored to identify a lead-related condition. Examples of the electrical properties that may be monitored include frequency-based transient characteristics, voltage across or current flowing through conductor 84 or some other characteristic derived from measured parameters such as an impedance of the conductor 84.

Another function of the limiter 124 may be to provide a stabilizing signal in the event that a lead-related condition is identified on the conductor 84. The limiter 124 may function to stabilize the sense path to preclude inappropriate logic and algorithmic decision making if the sense path is oscillating or noisy or exhibiting another non-physiological signal which could be disruptive. In that function, limiter 124 ties the conductor 84 to a defined threshold level to thereby prevent transmission and propagation of otherwise random signals which may arise due to a lead-related condition associated with the conductor, for example. Non-physiological oscillations are thereby inhibited and the signal path is stabilized. Otherwise, in the absence of a lead-related condition, the limiter 124 will not tie the conductor 84 to the threshold level to avoid any disruptive influences to the physiological signal on the conductor 84. In other words, the stabilizing limiter 124 will permit the physiological signal to be transmitted through the conductor 84 but otherwise provide a threshold (static) signal when the conductive pathway is not intact.

The arbitration element 112 receives the results of the analysis performed by recognition elements 126 and 128. Those results indicate whether the signal propagated through a given conductor is normal or is indicative of a lead-related condition as exhibited by a conductive pathway with erratic and indeterminate electrical behavior. The range for the characteristic properties of a normal electrical signal will be established by the dynamic syncopated source 130 and 132. Based on the processing results for each conductor 84, the arbitration element 112 selects one of the conductors 84 for coupling to the IMD sense circuitry and the selected conductor is designated as the primary conductor. Arbitration element 112 may also transmit the processing results of the analysis performed for each conductor 84 to the IMD for storage and additional processing such as trend analysis.

Sense path arbiter 106 may also include a frequency analyzer 130 for evaluating the frequency of the received signal. As such, the signal propagated through the conductor 84 will be evaluated to assess the frequency characteristics of the signal. The frequency analyzer 134 may provide an output of the frequency analysis, which includes such characteristics as an indication of whether the frequency of the signal falls within a given range, an amplitude of the signal, or duration of the signal, to the arbitration element 112. The characteristics of the signal as obtained through the frequency analysis may further aid in distinguishing between several lead-related conditions.

Arbitration element 112 determines whether to immediately accept the current sense signal on the primary path, whether to reconfigure, or whether to collect more information based on recent past information. Arbitration element 112 may instruct syncopated source 132 to change the window and other recognition criteria to gather data in a different range in time or other electrical criteria with different boundaries for the information. Arbitration element 112 may refine the criteria and continuously calibrate ranges until it is satisfied and ready to determine a final conclusion for reconfiguration.

Figure 11:
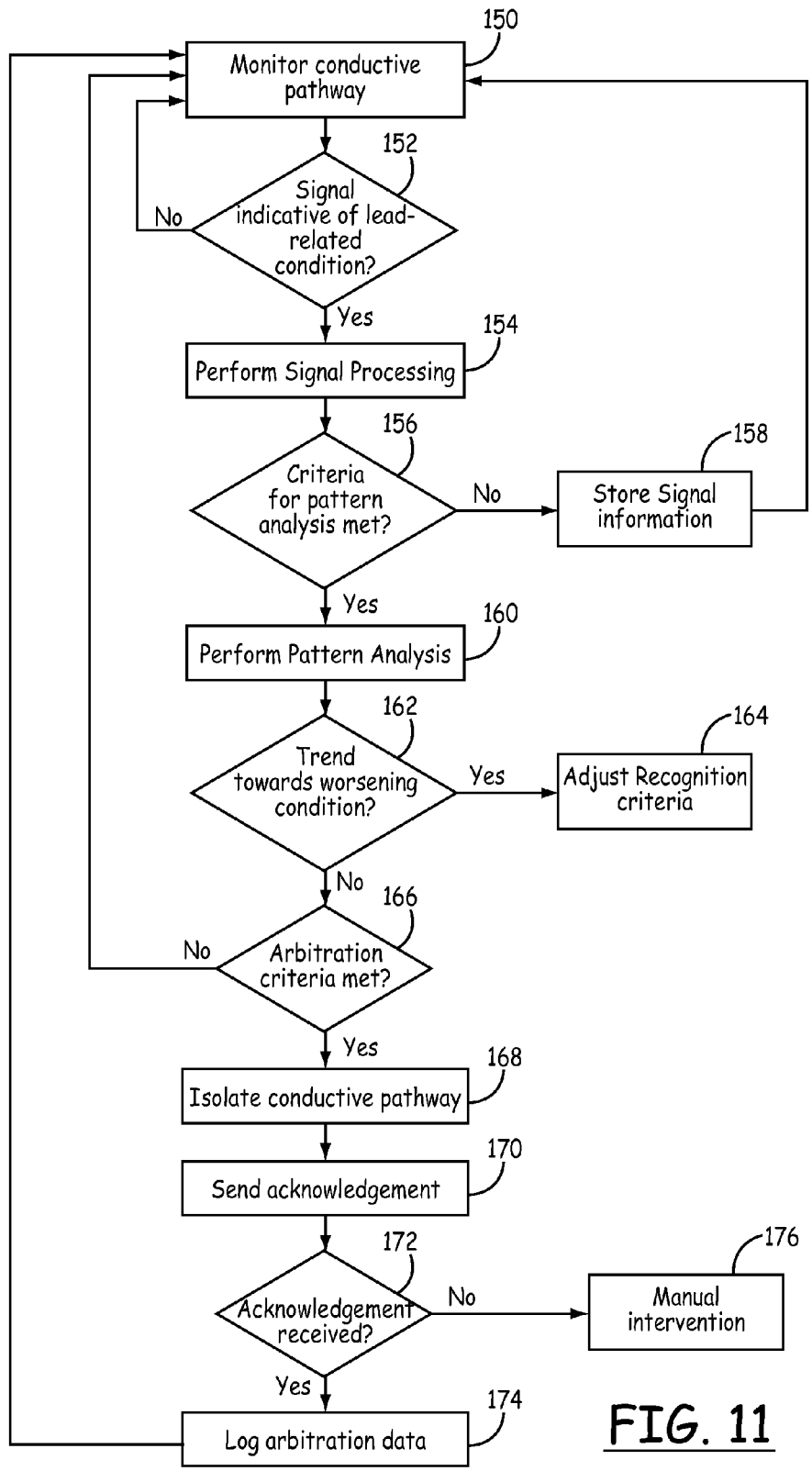
FIG. 11 is a flow diagram illustrating another exemplary embodiment of a method for detecting a lead-related condition of a medical electrical lead.

FIG. 11 illustrates a flow diagram of an illustrative method for dynamic reconfiguration of lead functionality in response to detecting a lead-related condition. The lead includes an electrode or sensing element for sensing electrical activity via two or more conductors that define a primary and secondary pathway and one of the sensed signals is transmitted to the IMD sense circuits based on processing performed as described in the preceding embodiments.

The method includes monitoring a set of conductive pathways associated with a given electrode or sensing element of a lead [150]. The conductive pathway may include a lead conductor and/or the insulation surrounding the conductor. The monitoring may be performed in real-time and/or continuously to enable the recognition of a lead-related condition immediately and thereby permit dynamic reconfiguration of the pathways for sustained sensing and/or therapy delivery functions. The method further involves determining whether a transient or other signal indicative of a lead-related condition [152] is present on the monitored pathways. Such an electrical signal may be one that deviates from a reference signal where the reference signal may be dynamically adjustable to provide a customizable reference signal for each individual patient. The dynamic adjustment of the reference signal will permit increased sensitivity of detection of a lead-related condition. In other words, the electrical signals indicative of a lead-related condition may be those that breach static upper and lower parametric limits or breach dynamic parametric limits where those limits are adjusted by the dynamic syncopated source 130 and 132 described above, for example.

The signals determined as having deviated from the parametric limits are processed to further obtain characteristic information such as the attributes for each individual transient including frequency of occurrence, duration, periods between individual transients, and burst frequencies [154]. As such, it can be determined whether the lead-related condition indicates one of a proximal end discontinuity, intermittent transient behavior having trains of discontinuity in various sequences and durations, or a static discontinuity whereby no conduction occurs along the path from the distal end to the proximal end.

Further, it is determined whether criteria for pattern analysis of the transient are met [156]. The criteria may include threshold crossings of one or more of the attributes obtained for each individual transient including frequency of occurrence, duration, periods between individual transients, and burst frequencies. If the criteria are not met, the transient data are stored and monitoring of the conductive pathways continues [158]. If the criteria are met, pattern analysis which may involve comparing the transient data to historical transient data is performed [160]. The pattern analysis may indicate a level of severity of the lead-related condition, or trends in the progression of the lead-related condition. Results of the analysis may be utilized in making adjustments to the reference signal such as through adjustments to the operating parameters for the dynamic syncopated sources 130 and 132. As such, the method involves performing a determination of whether the analysis indicates a worsening trend in the lead-related condition [162]. If so, adjustments are made to the recognition criteria for increased specificity and sensitivity to the detection method [164]. For example, the changes may include updating the reference signal, updating the recognition window or changing the detection scheme to focus on particular transient patterns. Specific changes to the window may include changes to the amplitude range and frequency range parameters such as 50,000 Hz to 100,000 Hz change and 0.1 mV to 100 mV change.

Next, the results of the analysis are evaluated to determine whether the arbitration criteria are met [166]. The evaluation involves determining the most optimal of the monitored electrical pathways (primary or secondary) as a function of any lead-related condition that may be present. If not met, the primary conductive pathway is determined to be the most optimal, and the lead monitoring proceeds with no configuration changes. Otherwise, if met, the conductor exhibiting a lead-related condition is isolated to prevent further use of the conductor for sensing and/or therapy delivery until an intervention is performed [168]. If the affected conductor is also the primary conductor, reconfiguration is performed to couple the electrode and/or sensing element to the most optimal electrical pathway. The reconfiguration may be performed as described above in the context of the sense path arbiter. An acknowledgment of the reconfiguration may be provided to the IMD and/or the principal arbiter (for embodiments having the principal-associate arbiters) [170]. The acknowledgment indicates that the arbitration and reconfiguration have successfully been performed. On receipt of the acknowledgement (YES in block 172), the arbitration data is logged and stored [174]. Otherwise, non-receipt of the acknowledgment will result in generation of an interrupt to the IMD for manual intervention [176].

While various exemplary lead assessment and lead-related condition detection techniques have been described, herein, in conjunction with lead 18—it should be understood that the disclosure is applicable to a multi-lead system including, for example, those depicted in FIGS. 1-4 having leads 20 and 22.

Functionality associated with one or more modules or units to support the various operations and functions described in this disclosure may be performed by separate hardware, software or firmware components, or integrated within common or separate hardware or software components in one or more devices. In addition, any of the described units, applications, modules or components may be implemented together or separately as discrete but interoperable logic devices. As such, the various functions of each module may in practice be combined, distributed or otherwise differently-organized in any fashion across the implantable systems of FIGS. 1-4. Thus, depiction of different features as modules or units is intended to highlight different functional aspects and does not necessarily imply that such modules or units must be realized by separate hardware or software components.

The techniques described in this disclosure, including those attributed to the implantable leads, IMD 16, programmer 24, or various constituent components, may be implemented, at least in part, in hardware, software, firmware or any combination thereof. For example, various aspects of the techniques may be implemented within one or more processors, including one or more microprocessors, digital signal processors (DSPs), application specific integrated circuits (ASICs), field programmable gate arrays (FPGAs), or any other equivalent integrated, analog, or discrete logic circuitry, as well as any combinations of such components, embodied in programmers, such as physician or patient programmers, stimulators, image processing devices or other devices. The term "processor" or "processing circuitry" may generally refer to any of the foregoing logic circuitry, alone or in combination with other logic circuitry, or any other equivalent circuitry.

When implemented in software, the functionality ascribed to the systems, devices and techniques described in this disclosure may be embodied as instructions on a computer-readable medium such as random access memory (RAM), read-only memory (ROM), non-volatile random access memory (NVRAM), electrically erasable programmable read-only memory (EEPROM), FLASH memory, magnetic data storage media, optical data storage media, or the like. The instructions may be executed to support one or more aspects of the functionality described in this disclosure.

Further, it should be appreciated that the exemplary embodiments are only examples, and are not intended to limit the scope, applicability, or configuration of the disclosure in any way. Rather, the foregoing detailed description will provide those skilled in the art with a convenient road map for implementing the exemplary embodiments. It should also be understood that various changes can be made in the function and arrangement of elements without departing from the scope of the disclosure as set forth in the appended claims and the legal equivalents thereof.

What is claimed is:

1. A method of detecting a lead-related condition associated with a medical electrical lead having an electrode and a plurality of conductors, wherein each of the plurality of conductors is coupled to the electrode, the method comprising:
   monitoring signals transmitted through the plurality of conductors;
   evaluating the signals for each of the conductors to detect an electrical property indicative of the lead-related condition;
   employing an arbitration scheme to select one of the conductors for propagation of a signal sensed by the electrode based on the evaluation; and
   coupling the selected conductor to sensing circuitry of an implantable medical device.

2. The method of claim 1, wherein the evaluation comprises comparing a voltage level of the signal for each of the plurality of conductors to a threshold level to detect a deviation from the threshold level.

3. The method of claim 1, wherein each one of the plurality of conductors includes a conductive pathway and further comprising filtering the conductive pathway of one of the plurality of conductors to permit transmission of signals having a target frequency.

4. The method of claim 3, further comprising analyzing monitored signals having a frequency other than the target frequency to obtain an electrical property.

5. The method of claim 4, wherein the analyzing comprises performing a pattern analysis of the monitored signals having a frequency other than the target frequency to obtain an electrical property.

6. The method of claim 1, further comprising classifying the lead-related condition based on a frequency range of the monitored signal.

7. The method of claim 1, wherein the evaluation further comprises identifying a leading indicator of a lead-related condition based on identifying a deviation of the monitored signal from a threshold signal.

8. The method of claim 1, wherein the threshold signal is dynamically adjustable as a function of the results of the evaluation.

9. The method of claim 1, wherein the evaluation further comprises identifying a leading indicator of a lead-related condition based on comparing the received signal to a template signal.

10. The method of claim 1, further comprising:
    defining a first conductor of the plurality of conductors as a primary conductor, and
    defining a second conductor of the plurality of conductors as a secondary conductor, and wherein employing the arbitration scheme comprises selecting the second conductor for transmission of the signal from the electrode in response to detecting the electrical property indicative of the lead-related condition associated with the first conductor.

11. The method of claim 1, wherein the evaluation of the signals from each of the conductors is performed simultaneously.

12. The method of claim 1, further comprising decoupling a given one of the plurality of conductors from the electrode in response to detecting the electrical property indicative of the lead-related condition associated with the given one of the plurality of conductors.

* * * * *